United States Patent
Aihara et al.

(10) Patent No.: US 9,494,513 B2
(45) Date of Patent: Nov. 15, 2016

(54) DETECTION METHOD OF TRANSMISSION LASER BEAM

(71) Applicant: DISCO CORPORATION, Tokyo (JP)

(72) Inventors: Chikara Aihara, Tokyo (JP); Tomohiro Endo, Tokyo (JP)

(73) Assignee: DISCO CORPORATION, Tokyo (JP)

( * ) Notice: Subject to any disclaimer, the term of this patent is extended or adjusted under 35 U.S.C. 154(b) by 0 days.

(21) Appl. No.: 14/938,318

(22) Filed: Nov. 11, 2015

(65) Prior Publication Data

US 2016/0153908 A1 Jun. 2, 2016

(30) Foreign Application Priority Data

Nov. 27, 2014 (JP) ................. 2014-239681

(51) Int. Cl.
*G01N 21/59* (2006.01)

(52) U.S. Cl.
CPC ..... *G01N 21/59* (2013.01); *G01N 2201/06113* (2013.01)

(58) Field of Classification Search
CPC .................... G01N 21/59; G01N 2201/06113
USPC ............ 438/33–34, 462; 355/30, 53, 72, 74
See application file for complete search history.

(56) References Cited

U.S. PATENT DOCUMENTS

| | | | | |
|---|---|---|---|---|
| 5,331,371 A * | 7/1994 | Mori | ................... | G03F 7/70066 355/53 |
| 5,374,291 A * | 12/1994 | Yabe | ....................... | C03C 15/00 347/70 |
| 9,093,519 B2 * | 7/2015 | Yamashita | ............ | H01L 21/302 |
| 2006/0062268 A1 * | 3/2006 | Saito | ...................... | B82Y 20/00 372/43.01 |
| 2006/0255022 A1 * | 11/2006 | Hoshino | ............ | B23K 26/0732 219/121.69 |
| 2007/0115450 A1 * | 5/2007 | Nagasaka | ........... | G03F 7/70341 355/72 |
| 2008/0047408 A1 * | 2/2008 | Oba | ........................ | H01L 21/78 83/39 |
| 2009/0078365 A1 * | 3/2009 | Suehara | ................ | B32B 37/223 156/249 |
| 2010/0087023 A1 * | 4/2010 | Endo | .................. | B23K 26/0626 438/33 |
| 2011/0159621 A1 * | 6/2011 | Endo | .................. | B23K 26/0057 438/34 |
| 2012/0309169 A1 * | 12/2012 | Endo | ....................... | H01L 21/78 438/462 |
| 2013/0120723 A1 * | 5/2013 | Ehrmann | ............ | G03F 7/70341 355/30 |
| 2014/0322847 A1 * | 10/2014 | Endo | ...................... | B23K 26/40 438/33 |

FOREIGN PATENT DOCUMENTS

JP 2012-059989 3/2012

* cited by examiner

*Primary Examiner* — Sang Nguyen

(74) *Attorney, Agent, or Firm* — Greer Burns & Crain, Ltd.

(57) ABSTRACT

A method of detecting a transmission laser beam is disclosed. A laser beam of a wavelength having a transparency to a plate-shaped workpiece having a first face and a second face is irradiated upon the workpiece from the first face side with a focal point of the laser beam positioned in the inside of the workpiece. The laser beam is detected after it has passed through the workpiece to the second face side. A photosensitive sheet is positioned to hold the workpiece on a holding face of a chuck table. A photosensitive layer between the sheet and the workpiece is opposed to the second face of the workpiece. The laser beam is irradiated from the first face side of the workpiece, and the state of the transmission laser beam from a photosensitive reaction region formed in the photosensitive layer of the photosensitive sheet is confirmed.

14 Claims, 7 Drawing Sheets ature of the laser beam cannot be confirmed directly, the influence of leak light is confirmed from a
DETECTION METHOD OF TRANSMISSION LASER BEAM

BACKGROUND OF THE INVENTION

Field of the Invention

The present invention relates to a detection method of a transmission laser beam for detecting, when a laser beam of a wavelength having a transparency to a workpiece is irradiated upon the workpiece, the laser beam having passed through the workpiece.

Description of the Related Art

A processing method is known wherein a laser beam of a wavelength having a transparency to a plate-shaped workpiece such as a semiconductor wafer or an optical device wafer is irradiated upon the workpiece with a focal point thereof positioned in the inside of the workpiece to form a modified layer, which serves as a start point of break, in the inside of the workpiece and then external force is applied to the workpiece to divide the workpiece into individual chips. In this processing method, although almost all of the laser beam is absorbed in the inside of the workpiece, so-called leak light appears which passes to a second face of the workpiece on the opposite side to an irradiation face (first face) of the workpiece by the laser beam (for example, refer to Japanese Patent Laid-Open No. 2012-59989).

A laser beam is oscillated by a laser oscillator and irradiated upon a workpiece through an optical system, which is configured from various optical parts, and a condenser. However, depending upon setting of the optical system, a cross section of a laser beam sometimes exhibits a distorted intensity distribution asymmetric in the radial direction. If such a laser beam as just described is used to process a workpiece, then a modified layer which is less liable to break may be formed or the appearance range of leak light may expand to such a degree that the leak light protrudes from a scheduled division line and has a bad influence on a device.

SUMMARY OF THE INVENTION

Conventionally, since leak light cannot be confirmed directly, the influence of leak light is confirmed from a fraction defective of device chips. However, since evaluation of electric characteristics of each device chip requires a very great number of man-hours, it is not easy to confirm the state of leak light.

Therefore, it is an object of the present invention to provide a detection method of a transmission laser beam by which the state of leak light can be confirmed readily at a low cost.

In accordance with an aspect of the present invention, there is provided a detection method of a transmission laser beam for irradiating a laser beam of a wavelength having a transparency to a plate-shaped workpiece having a first face and a second face opposite to the first face upon the workpiece from the first face side with a focal point of the laser beam positioned in the inside of the workpiece to detect laser beam which has passed through the workpiece to the second face side. The detection method includes: a photosensitive sheet positioning step of holding the workpiece on a holding face of a chuck table with a photosensitive sheet, which has a photosensitive layer, interposed therebetween such that the photosensitive layer is opposed to the second face of the workpiece; a laser beam irradiation step of irradiating, after the photosensitive sheet positioning step is performed, the laser beam from the first face side of the workpiece; and a confirmation step of confirming, after the laser beam irradiation step is performed, a state of transmission laser beam from a photosensitive reaction region formed in the photosensitive layer of the photosensitive sheet.

Preferably, at the photosensitive sheet positioning step, the photosensitive sheet is adhered to the second face of the workpiece with a layer of liquid, which has a transparency, interposed therebetween.

According to the present invention, by observing the photosensitive sheet after the laser beam is irradiated upon the workpiece from the first face side with the photosensitive layer of the photosensitive sheet positioned so as to be opposed to the second face of the workpiece, the state of the transmission laser beam (leak light) when the laser beam is irradiated upon the first face of the workpiece can be confirmed readily and besides at a low cost. As a result, selection of processing conditions by which leak light can be suppressed can be performed efficiently.

Depending upon the type of the photosensitive layer, the energy distribution of leak light can be confirmed from a variation in color of the photosensitive layer. Therefore, the detection method of a transmission laser beam of the present invention can be applied to a check of the energy distribution of a laser beam irradiated upon a workpiece, and is very effective also for adjustment of setting of an optical system.

The above and other objects, features and advantages of the present invention and the manner of realizing them will become more apparent, and the invention itself will best be understood from a study of the following description and the appended claims with reference to the attached drawings showing a preferred embodiment of the invention.

DETAILED DESCRIPTION OF THE PREFERRED EMBODIMENT

Figure 1:
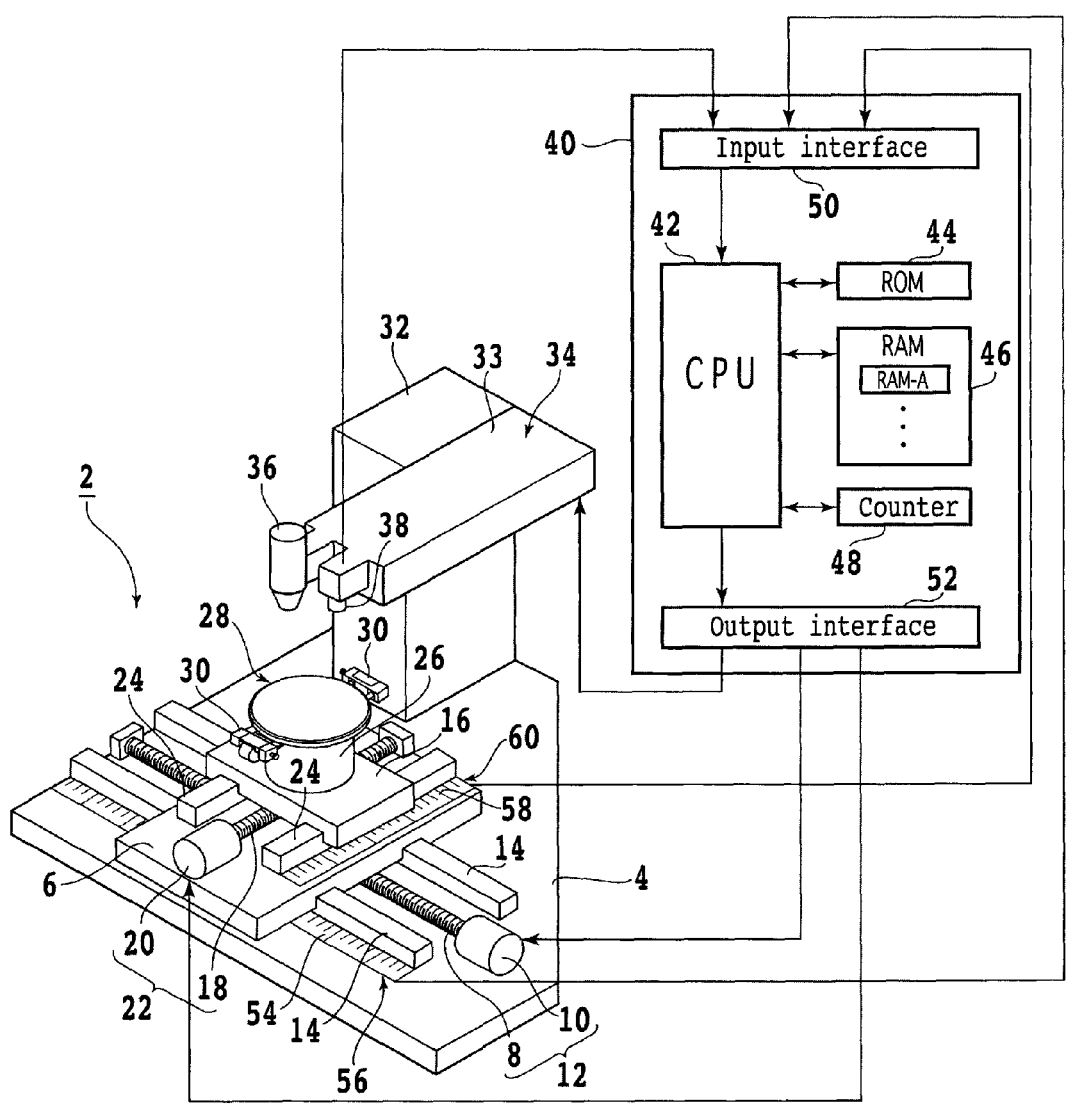
FIG. 1 is a perspective view of a laser processing apparatus suitable to perform a detection method of a transmission laser beam according to the present invention.

In the following, an embodiment of the present invention is described in detail with reference to the drawings. Referring to FIG. 1, there is shown a perspective view of a laser processing apparatus 2 suitable to perform a detection method of a transmission laser beam according to the present invention. The laser processing apparatus 2 includes a first slide block 6 mounted for movement in an X-axis direction on a stationary base 4. The first slide block 6 is moved in a processing feeding direction, namely, in the X-axis direction, along a pair of guide rails 14 by processing feeding means 12 configured from a ball screw 8 and a stepping motor 10.

A second slide block 16 is mounted for movement in a Y-axis direction on the first slide block 6. In particular, the second slide block 16 is moved in an indexing direction, namely, in the Y-axis direction, along a pair of guide rails 24 by indexing feeding means 22 configured from a ball screw 18 and a stepping motor 20. A chuck table 28 is mounted on the second slide block 16 through a cylindrical support member 26 such that the chuck table 28 is rotatable and is movable in the X-axis direction and the Y-axis direction by the processing feeding means 12 and the indexing feeding means 22.

Figure 2:
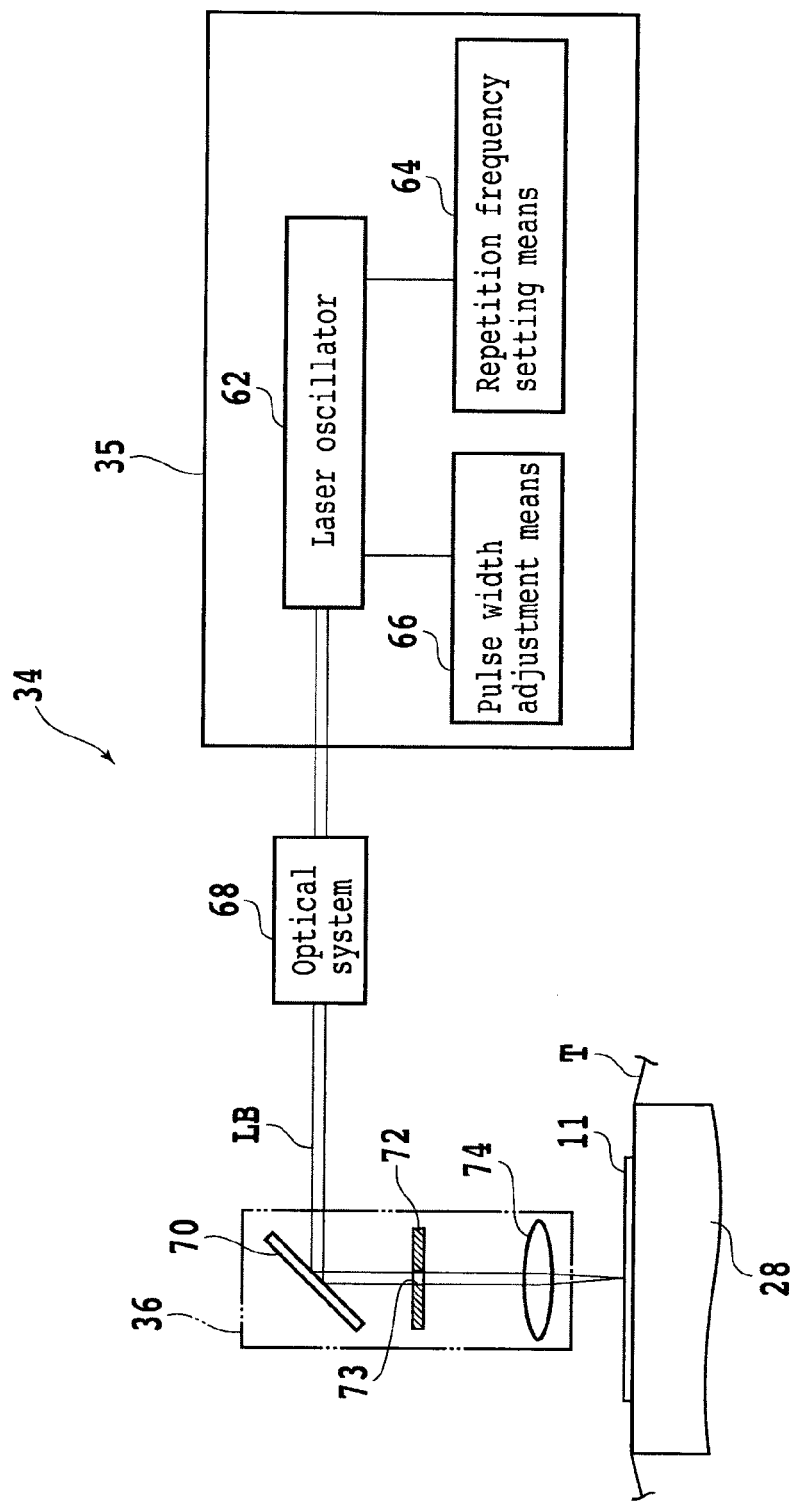
FIG. 2 is a block diagram of a laser beam generation unit.

A clamp 30 is provided on the chuck table 28 such that it clamps an annular frame which supports a semiconductor wafer held under suction by the chuck table 28 through a dicing table. A column 32 is provided uprightly on the stationary base 4, and a laser beam irradiation unit 34 is attached to the column 32. The laser beam irradiation unit 34 includes a laser beam generation unit 35 accommodated in a casing 33, an optical system 68 and a condenser 36 attached to an end of the casing 33 as depicted in FIG. 2.

The laser beam generation unit 35 includes a laser oscillator 62 which oscillates a YAG laser or a YVO4 laser, repetition frequency setting means 64, and pulse width adjustment means 66. Though not particularly depicted, the laser oscillator 62 has a Brewster window, and a laser beam emitted from the laser oscillator 62 is that of linearly polarized light.

Figure 3:
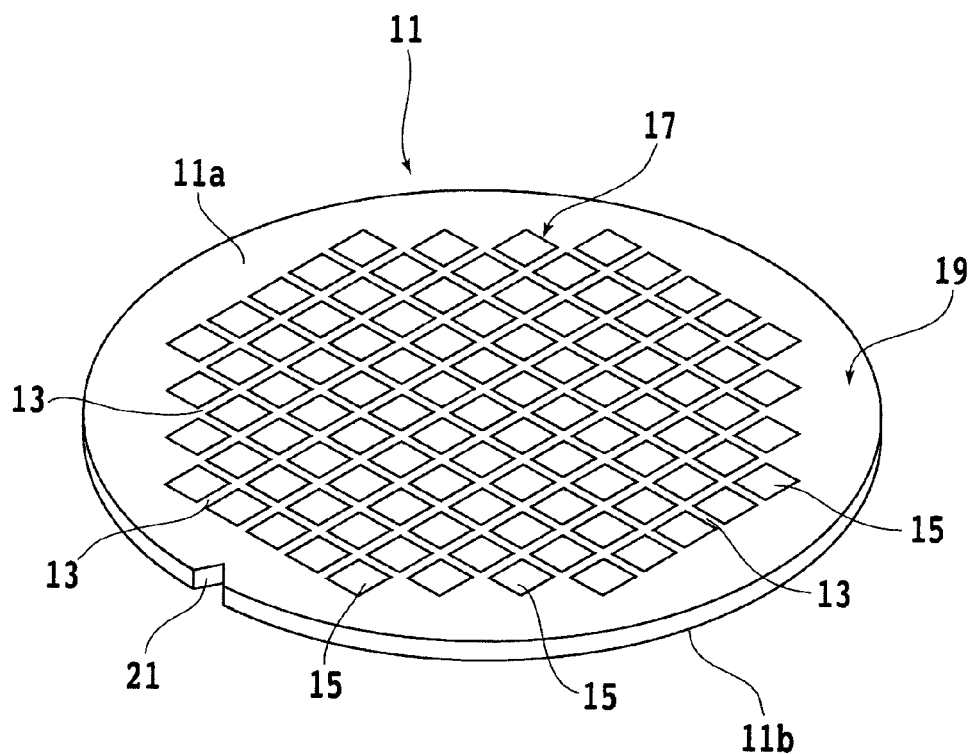
FIG. 3 is a perspective view of the front face side of a semiconductor wafer.

A pulse laser beam LB oscillated from the laser oscillator 62 of the laser beam generation unit 35 has a wavelength having a transparency to a semiconductor wafer 11 depicted in FIG. 3 and has, for example, a wavelength of 1064 nm. The pulse laser beam LB oscillated from the laser oscillator 62 of the laser beam generation unit 35 passes through the optical system 68 configured from a plurality of optical parts and is made incident to the condenser 36. The pulse laser beam LB made incident to the condenser 36 is reflected by a mirror 70, passes through a pinhole 73 of a mask 72 and is irradiated upon the semiconductor wafer 11 held on the chuck table 28 by a condensing lens 74.

Referring back to FIG. 1, an image pickup unit 38 is disposed at an end portion of the casing 33 such that it detects a processing region to be laser-processed in an aligned relationship in the X-axis direction with the condenser 36. The image pickup unit 38 includes an image pickup element such as an ordinary CCD element for picking up an image of a processing region of a semiconductor wafer by visible light. The image pickup unit 38 further includes infrared irradiation means for irradiating infrared rays on the semiconductor wafer, an optical system for capturing the infrared rays irradiated by the infrared irradiation means, and infrared image pickup means configured from an infrared image pickup element such as an infrared CCD element which outputs an electric signal corresponding to the infrared rays captured by the optical system. The picked up image is transmitted to a controller (control means) 40.

The controller 40 is configured from a computer and includes a central processing unit (CPU) 42 for performing arithmetic operation processing in accordance with a control program, a read-only memory (ROM) 44 in which the control program and so forth are filed, a readable and writable random access memory (RAM) 46 into which arithmetic operation results and so forth are filed, a counter 48, an input interface 50 and an output interface 52.

Processing feeding amount detection means 56 is configured from a linear scale 54 disposed along the guide rails 14 and a reading head not depicted disposed on the first slide block 6. A detection signal of the processing feeding amount detection means 56 is inputted to the input interface 50 of the controller 40.

Indexing feeding amount detection means 60 is configured from a linear scale 58 disposed along the guide rails 24 and a reading head not depicted disposed on the second slide block 16. A detection signal of the indexing feeding amount detection means 60 is inputted to the input interface 50 of the controller 40.

Also an image signal picked up by the image pickup unit 38 is inputted to the input interface 50 of the controller 40. From the output interface 52 of the controller 40, control signals are outputted to the stepping motor 10, stepping motor 20, laser beam irradiation unit 34 and so forth.

Referring to FIG. 3, there is shown a perspective view of a front face side of the semiconductor wafer 11 as an example of a plate-shaped workpiece which is a processing target of the laser processing apparatus 2. On a front face 11a of the semiconductor wafer 11 (hereinafter referred to sometimes as wafer simply), devices 15 such as ICs or LSIs are formed in regions partitioned by a plurality of scheduled division lines (streets) 13 formed in a grating pattern. The semiconductor wafer 11 has a device region 17 in which the plurality of devices 15 are formed, and a peripheral redundant region 19 surrounding the device region 17. On an outer periphery of the semiconductor wafer 11, a notch 21 is formed which serves as a mark indicative of a crystal orientation of the semiconductor wafer 11 formed from silicon.

In the following, a detection method of a transmission laser beam according to the embodiment of the present invention by the laser processing apparatus 2 configured in such a manner as described is described with reference to FIGS. 4A to 7B. In the transmission laser beam detection method of the present embodiment, a photosensitive sheet positioning step of holding the semiconductor wafer 11 under suction by the chuck table 28 of the laser processing apparatus 2 with a photosensitive sheet 23 interposed therebetween while a photosensitive layer 27 formed on a base material 25 of the photosensitive sheet 23 is first opposed to the front face (second face) 11a of the semiconductor wafer 11 as depicted in FIGS. 4A and 4B is performed.

Figure 4A:
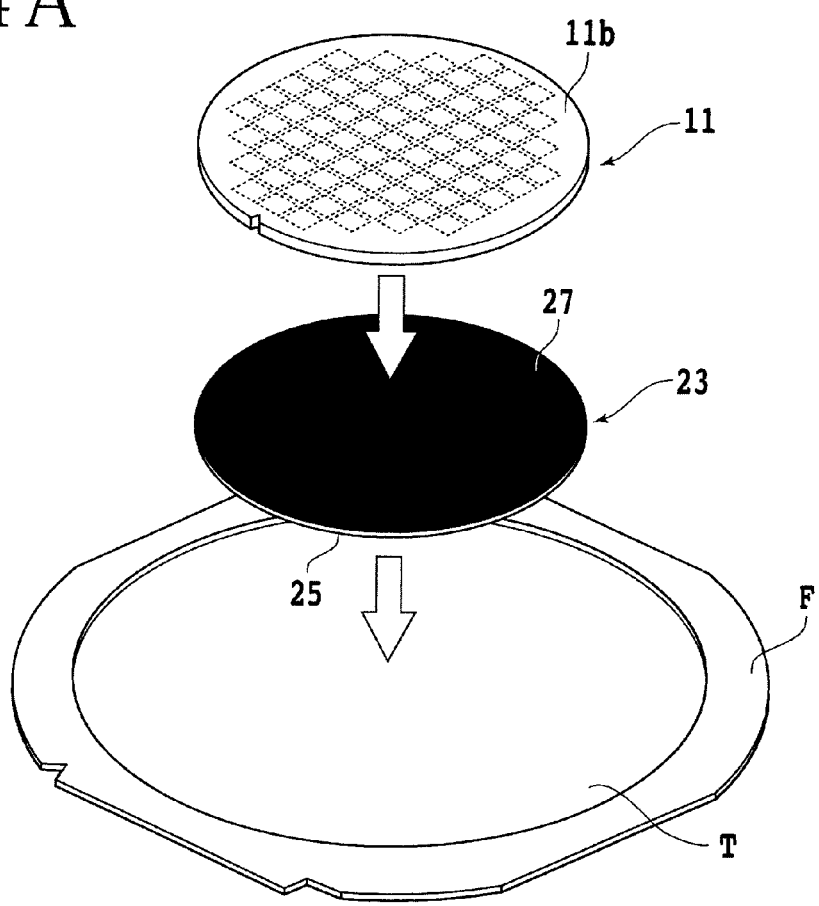
FIG. 4A is an exploded perspective view illustrating a photosensitive sheet positioning step.
Figure 4B:
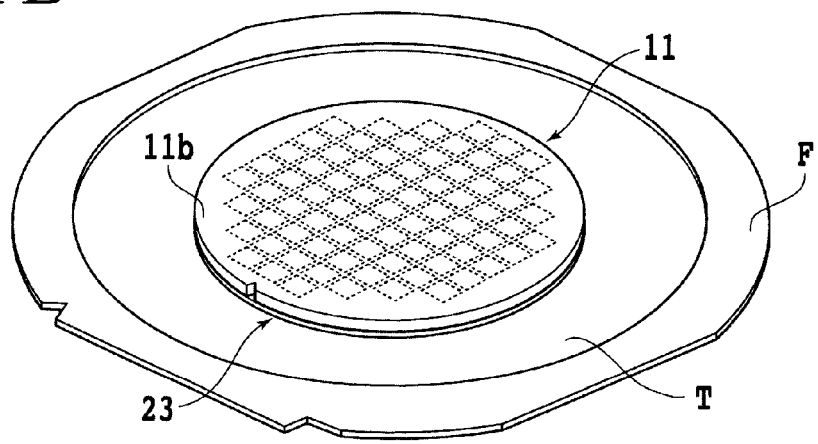
FIG. 4B is a perspective view illustrating the photosensitive sheet positioning step.

At the photosensitive sheet positioning step, the photosensitive layer 27 of the photosensitive sheet 23 is adhered to the front face (second face) 11a of the semiconductor wafer 11 with a layer of liquid, which has transparency, interposed therebetween as depicted in FIG. 4A, and the base material 25 of the photosensitive sheet 23 is pasted to a dicing sheet T attached at its outer periphery to an annular frame F as depicted in FIG. 4B.

Consequently, the semiconductor wafer 11 is supported on the annular frame F with the photosensitive sheet 23 and the dicing sheet T interposed therebetween, and a rear face (first face) 11b of the semiconductor wafer 11 is exposed. As the layer of transparent liquid, a water-soluble resin can be used. As the photosensitive sheet 23, for example, an alignment sheet ZAP-IT manufactured by KENTEK CORP and compatible with 5 mJ/cm$^2$ to 20 J/cm$^2$ can be used.

Figure 5:
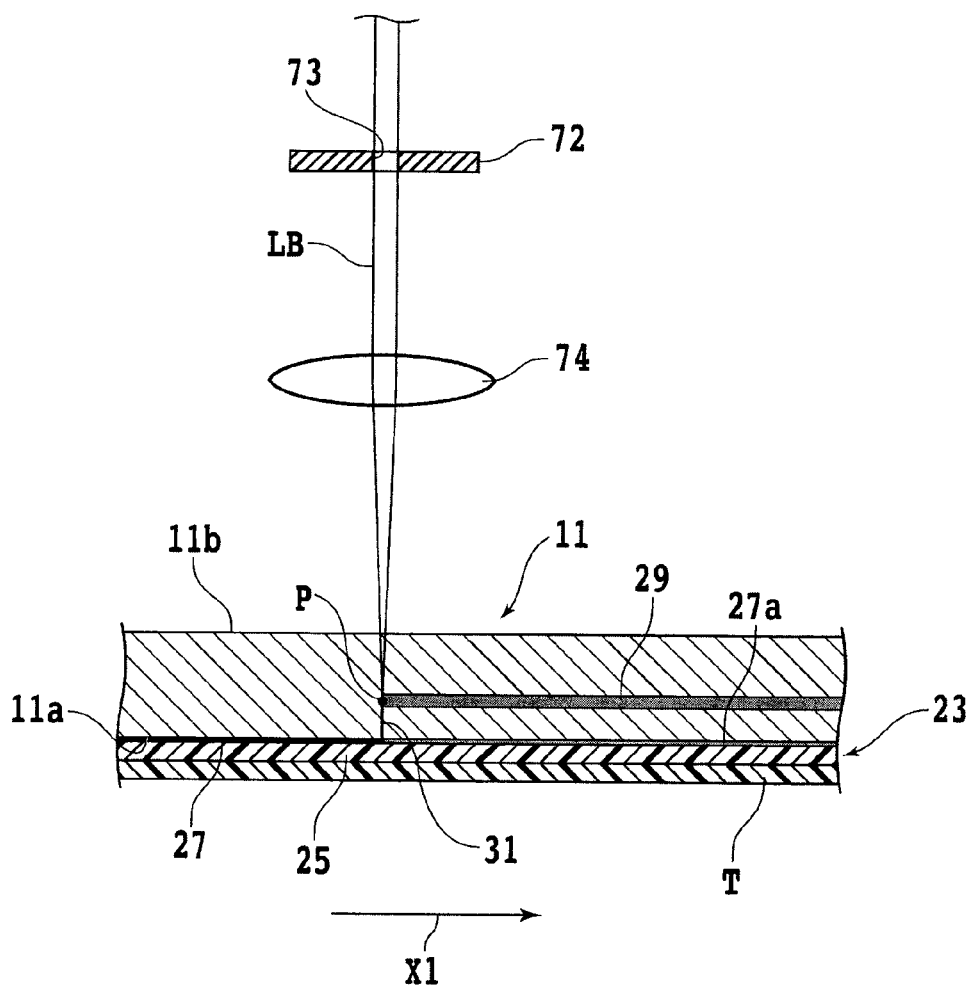
FIG. 5 is a sectional view depicting a laser beam irradiation step.

After the photosensitive sheet positioning step is performed, a laser beam irradiation step of irradiating the pulse laser beam LB of a wavelength having a transparency to the semiconductor wafer 11 with the focal point P thereof positioned in the inside of the semiconductor wafer 11 from the rear face (first face) 11b side of the semiconductor wafer 11 as depicted in FIG. 5 is performed. The pulse laser beam LB having a transparency to the semiconductor wafer 11 has a wavelength of, for example, 1064 nm.

If the chuck table 28 is processing fed in the direction of an arrow mark X1 while the pulse laser beam LB is irradiated from the rear face 11b side of the semiconductor wafer 11 with the focal point P thereof positioned in the inside of the semiconductor wafer 11, then a modified layer 29 is formed in the inside of the semiconductor wafer 11 by multiphoton absorption. Although major part of the pulse laser beam LB is absorbed at the focal point P, part of the pulse laser beam LB is emitted as leak light (transmission laser beam) 31 from the front face (second face) 11a of the semiconductor wafer 11.

Figure 6A:
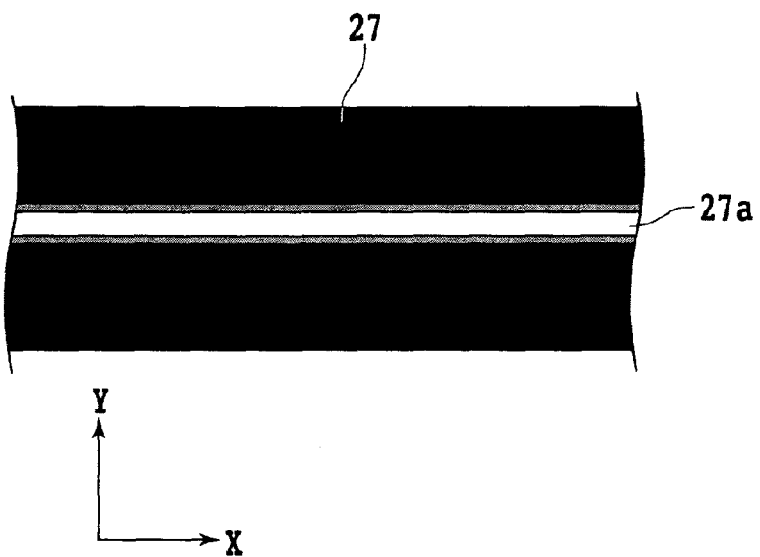
FIG. 6A is a plan view depicting an example of a photosensitive reaction of a photosensitive layer by leak light.
Figure 6B:
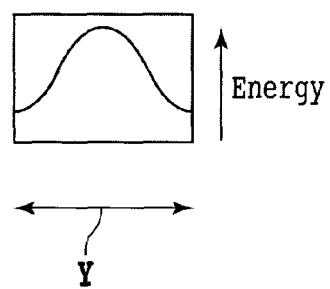
FIG. 6B is a view depicting an energy distribution of leak light.

The photosensitive layer 27 of the photosensitive sheet 23 adhered to the front face (second face) 11a of the semiconductor wafer 11 reacts with the leak light 31, and consequently, a photosensitive reaction region 27a is formed in the photosensitive layer 27. The photosensitive reaction region 27a is formed symmetrically in the Y axis direction with respect to the center of the leak light 31 as depicted in FIG. 6A. In FIG. 6A, a blank portion indicates a region in which the intensity distribution of leak light is high while a gray portion indicates a region in which the intensity distribution of leak light is low. In particular, as depicted in FIG. 6B, the intensity distribution in a cross section of the transmission laser beam (leak light) 31 is symmetrical in a radial direction with respect to the center of the leak light 31. In this case, the pulse laser beam LB is irradiated upon the semiconductor wafer 11 with the center thereof aligned with the center of the pinhole 73 formed on the mask 72. Consequently, the optical system 68 is set optimally.

Figure 7A:
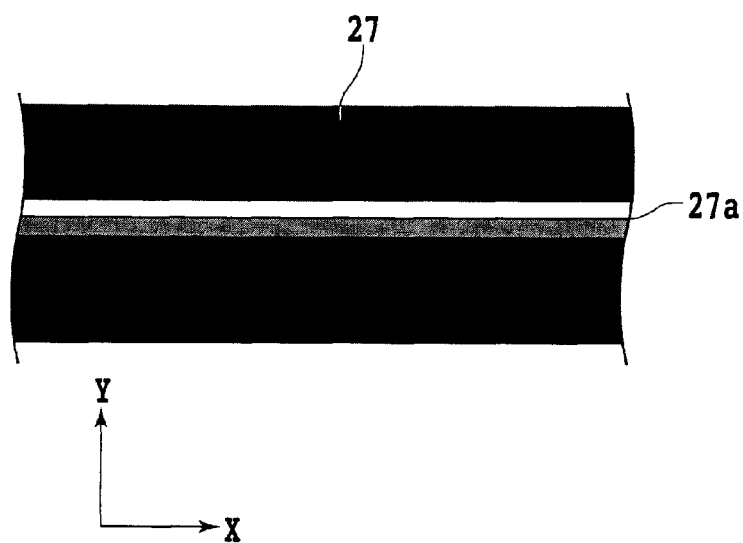
FIG. 7A is a plan view depicting another example of a photosensitive reaction of a photosensitive layer by leak light.
Figure 7B:
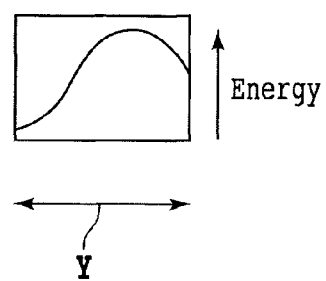
FIG. 7B is a view depicting an energy distribution of leak light.

On the other hand, if the intensity distribution of the leak light 31 is one-sided as depicted in FIG. 7B, then the photosensitive reaction region 27a of the photosensitive layer 27 exhibits such a state as depicted in FIG. 7A, and the state of the leak light 31 can be confirmed by observing the photosensitive reaction region 27a. Where the intensity distribution of leak light (transmission laser beam) is not symmetrical with respect to the center of the leak light 31 in this manner, it can be decided that this arises from the fact that the center of the pulse laser beam LB irradiated upon the semiconductor wafer 11 is not aligned with the center of the pinhole 73 formed on the mask 72. Therefore, the optical parts of the optical system 68 are adjusted so that the center of the pulse laser beam LB is aligned with the center of the pinhole 73.

After the setting of the optical parts of the optical system 68 is adjusted, the photosensitive reaction region 27a of the photosensitive layer 27 is observed again. Thus, adjustment of the optical system 68 is repeated until the intensity distribution of the leak light 31 becomes symmetrical in a radial direction with respect to the center of the leak light 31.

In the foregoing description of the embodiment, an example wherein the detection method of a transmission laser beam of the present invention is applied to the semiconductor wafer 11 is described. However, the workpiece is not limited to the semiconductor wafer 11, and the detection method of a transmission laser beam of the present invention can be applied similarly to other plate-shaped workpieces such as an optical device wafer. Further, the detection method of a transmission laser beam of the present invention can be used also for confirmation of misalignment between various optical parts and a laser beam in addition to the positioning confirmation between a laser beam and a pinhole.

The present invention is not limited to the details of the above described preferred embodiment. The scope of the invention is defined by the appended claims and all changes and modifications as fall within the equivalence of the scope of the claims are therefore to be embraced by the invention.

What is claimed is:

1. A detection method of a transmission laser beam for irradiating a laser beam of a wavelength having a transparency to a plate-shaped workpiece having a first face and a second face opposite to the first face upon the workpiece from the first face side with a focal point of the laser beam positioned in the inside of the workpiece to detect laser beam which has passed through the workpiece to the second face side, comprising:

a photosensitive sheet positioning step of holding the workpiece on a holding face of a chuck table with a photosensitive sheet, which has a photosensitive layer, interposed therebetween such that the photosensitive layer is opposed to the second face of the workpiece;

a laser beam irradiation step of irradiating, after the photosensitive sheet positioning step is performed, the laser beam from the first face side of the workpiece; and a confirmation step of confirming, after the laser beam irradiation step is performed, whether the intensity distribution of the transmission laser beam is symmetrical with respect to the center of the transmission laser beam from a photosensitive reaction region formed in the photosensitive layer of the photosensitive sheet.

2. The detection method of a transmission laser beam according to claim 1, wherein, at the photosensitive sheet positioning step, the photosensitive sheet is adhered to the second face of the workpiece with a layer of liquid, which has a transparency, interposed therebetween.

3. The detection method of a transmission laser beam according to claim 1, wherein the second face of the workpiece includes a plurality of devices thereon that are separated from each other by a plurality of division lines formed in a grating pattern.

4. The detection method of a transmission laser beam according to claim 1, wherein said laser beam irradiation step results in the formation of a modified layer within the workpiece.

5. The detection method of a transmission laser beam according to claim 4, wherein said modified layer does not extend to either the first or second faces of the workpiece.

6. The detection method of a transmission laser beam according to claim 1, wherein said confirmation step includes confirming the positioning of a mask including a pinhole therein, whereby the laser beam is passed through the pinhole.

7. The detection method of a transmission laser beam according to claim 6, further comprising an adjusting step of adjusting the alignment of the mask based on the results of said confirmation step.

8. A detection method of a transmission laser beam for irradiating a laser beam of a wavelength having a transparency to a plate-shaped workpiece having a first face and a second face opposite to the first face upon the workpiece from the first face side with a focal point of the laser beam positioned in the inside of the workpiece to detect laser beam which has passed through the workpiece to the second face side, comprising:

a photosensitive sheet positioning step of holding the workpiece on a holding face of a chuck table with a photosensitive sheet, which has a photosensitive layer, interposed therebetween such that the photosensitive layer is opposed to the second face of the workpiece, wherein the second face of the workpiece includes a plurality of devices thereon that are separated from each other by a plurality of division lines formed in a grating pattern and further wherein the photosensitive sheet is in contact with the second face of the workpiece;

a laser beam irradiation step of irradiating, after the photosensitive sheet positioning step is performed, the laser beam from the first face side of the workpiece; and a confirmation step of confirming, after the laser beam irradiation step is performed, whether the intensity distribution of the transmission laser beam is symmetrical with respect to the center of the transmission laser beam from a photosensitive reaction region formed in the photosensitive layer of the photosensitive sheet.

9. The detection method of a transmission laser beam according to claim 8, wherein said devices are formed in a device region of the workpiece, and further wherein said device region is surrounded by a peripheral redundant region of the wafer.

10. The detection method of a transmission laser beam according to claim 9, wherein said photosensitive layer is at least positioned in an area corresponding to the device region.

11. The detection method of a transmission laser beam according to claim 9, wherein said photosensitive layer is at positioned in an area corresponding to both the device region and the peripheral redundant region.

12. A detection method of a transmission laser beam for irradiating a laser beam of a wavelength having a transparency to a plate-shaped workpiece having a first face and a second face opposite to the first face upon the workpiece from the first face side with a focal point of the laser beam positioned in the inside of the workpiece to detect laser beam which has passed through the workpiece to the second face side, comprising:

a photosensitive sheet positioning step of holding the workpiece on a holding face of a chuck table with a photosensitive sheet, which has a photosensitive layer, interposed therebetween such that the photosensitive layer is opposed to the second face of the workpiece;

a laser beam irradiation step of irradiating, after the photosensitive sheet positioning step is performed, the laser beam from the first face side of the workpiece; and a confirmation step of confirming, after the laser beam irradiation step is performed, whether the intensity distribution of the transmission laser beam is symmetrical with respect to the center of the transmission laser beam from a photosensitive reaction region formed in the photosensitive layer of the photosensitive sheet, wherein said confirmation step also includes confirming the positioning of at least one optical part included in an optical system, whereby the laser beam is passed through the optical part.

13. The detection method of a transmission laser beam according to claim 12, wherein, at the photosensitive sheet positioning step, the photosensitive sheet is adhered to the second face of the workpiece with a layer of liquid, which has a transparency, interposed therebetween.

14. The detection method of a transmission laser beam according to claim 13, further comprising an adjusting step of adjusting the alignment of the optical part based on the results of said confirmation step.

\* \* \* \* \*